United States Patent [19]

Rosenfeld

[11] Patent Number: 5,827,191
[45] Date of Patent: Oct. 27, 1998

[54] METHOD AND A DEVICE FOR MONITORING MILK VOLUME DURING BREAST FEEDING

[76] Inventor: Haim Rosenfeld, 1/6 Hatotchan St., Jerusalem, Israel

[21] Appl. No.: 724,514

[22] Filed: Sep. 30, 1996

[30] Foreign Application Priority Data

Sep. 28, 1995 [IL] Israel ........................................ 115456

[51] Int. Cl.[6] ........................................................ A61B 6/00
[52] U.S. Cl. ........................... 600/476; 128/898; 73/861
[58] Field of Search ................................. 128/774, 664, 128/665, 897, 898, 630; 604/74, 317, 346, 355; 73/861, 861.02, 861.04, 861.77; 356/138, 399, 400; 600/300, 587, 473, 476

[56] References Cited

U.S. PATENT DOCUMENTS

| | | | |
|---|---|---|---|
| 196,594 | 10/1877 | Patch | 604/346 |
| 1,032,518 | 7/1912 | Thieringer | 604/346 |
| 4,799,922 | 1/1989 | Beer et al. | 604/346 |
| 4,851,666 | 7/1989 | Anderson et al. | 73/861.77 |
| 5,388,466 | 2/1995 | Teunissen | 73/861.77 |
| 5,542,921 | 8/1996 | Meyers et al. | 604/346 |
| 5,638,174 | 6/1997 | Henderson | 73/861.77 |

*Primary Examiner*—Jennifer Bahr
*Assistant Examiner*—Bryan K. Yarnell
*Attorney, Agent, or Firm*—Lowe Hauptman Gopstein & Berner

[57] ABSTRACT

A method for monitoring a volume of milk during breast feeding utilizes an elastic nipple shaped cover applied over a nipple area of a woman's breast with holes in the cover positioned above the nipple area for passage of milk to the baby's mouth. A micro measurement volume sensor is located in a space between the nipple and the elastic cover holes to measure the volume of milk flowing therethrough. Data from the micro measurement volume sensor is converted into a calibrated volumetric equivalent corresponding to milk volume data indicative of the milk volume. This milk volume data may be displayed in real time on a display monitor.

21 Claims, 4 Drawing Sheets

METHOD AND A DEVICE FOR MONITORING MILK VOLUME DURING BREAST FEEDING

FIELD OF THE INVENTION

The present invention relates to a method for monitoring milk volume during breast feeding and also to a device for the real time monitoring of same.

BACKGROUND OF THE INVENTION

A well known method of determining milk volume during breast feeding involves measurement of a baby's weight before and after feeding. Apart from the obvious inconvenience, the volume of milk measured by this method can be so small relative to the babies weight as to require the use of expensive accurate digital weight scales. The sensitivity of a digital scale is often disturbed by the normal body functions of the infant (i.e. moving, crying, breathing, heart beat, defication, mincteration, etc.). Moreover, this well known method can not provide any real time information about the milk volumes consumed by the baby at every second during breast feeding. There is a need of method and a device for the real time monitoring of accurate milk volumes during breast feeding. The mother wants to know how much milk the baby had at every moment, and also sometimes the medical personel staff wants to know. Suprisingly, the method and the device according to the present invention overcomes the above mentioned disadvantages and opens up a new dimension of monitoring the milk volume in real time.

SUMMARY OF THE INVENTION

The present invention relates to a method for monitoring the milk volume during breast feeding in real time. The present invention also relates to a device for the real time monitoring of the milk volume during breast feeding.

The method according to the present invention for monitoring the milk volume during breast feeding consists of: (a) applying over the nipple area an elastic cover designed like a nipple with holes above the real nipple for milk passage to the baby's mouth wherein at the bottom of the cover, in the space between the nipple and the cover holes, there is a micro measurement volume sensor for measuring the milk volume which flows therethrough, (b) converting the data from the micro measurment volume sensor into a calibrated volumetric equivalent for milk, and (c) presenting the milk volume data on a display monitor.

The device according to the present invention comprises a flexible elastic nipple cover with holes above the nipple, with the cover designed like a. A micro measurement volume sensor is attached to the cover at the bottom of the cover above the nipple for measuring the milk volume passing through the space between the nipple and the cover. A data interpretation unit is connected to the volume sensor for counting, integrating, normalizing, and interpreting the volume sensor output to the volumetric equivalent for milk. A data display monitor connected to the said data interpretation unit displaying the volume of the milk measured.

In its preferred embodiment, the micro measurement volume sensor has a free spinning propeller having a rotation which is sensed preferably with optical sieves transmitting light to the sensor and receiving back the modified light. Stated differently, the method for monitoring milk volume during breast feeding according to the present invention comprises the steps of placing a micro measurement volume sensor between the mother's nipple and the baby's mouth through which all of the exuded milk passes, converting the data from the sensor into its correct interpretation in volumetric units for milk; and presenting the milk volume data on a display monitor.

More specifically, a micro measurement volume sensor in the space between the mother's nipple and the baby's mouth through which all of the exuded milk passes. Placement is accomplished by applying over the nipple area an elastic cover designed like a nipple with holes above the real nipple for milk passage to the baby's mouth. At the bottom of the cover in the space between the nipple and the cover holes there is the micro measurement volume sensor that measures the volume of milk flowing through it.

The space is preferably an enclosed channel in which a free spinning propeller or a free spinning disk rotates according to the volume of milk which flows past it. This induced rotation can be optically monitored and the results thereafter interpreted. This interpretation requires calibration due to the shape of the channel, the nature of the rotation, the irregularity of the milk flow rate, temperature, viscosity, opaque variability, etc.

The micro measurement volume sensor in the preferred embodiment of the invention is a fluid flow volume meter wherein the free spinning of the propeller or the disk is measured when the rotation is sensed by reflecting the flow light in optic guide path or by changing the polarization of the flow of light in the optic guide path or by interrupting the flow of light in optic guide path.

In a preferred embodiment of the invention there is provided a unit for interpreting the micro measurement sensor data wherein light originating in the unit traverses a fiber optic cable which is connected to the micro measurement sensor where the light is interrupted (or modified) and returned along a different fiber optic cable or along the same fiber optic cable.

The unit for interpreting the sensor data measures the returned light with a sensor such as a photo electric cell used as a stroboscopic counter or by using standard interferrmetric methods. Thus, counting the number of rotations of the free spinning unit of the sensor, being either a propeller or a disk, and if necessary measuring the speed of rotation associated with each rotation or partial rotation, this unit can now perform the necessary calculations to normalize the received data against calibration data and thus present the results on any display monitor. In one embodiment the display monitor can show a simple numerical result corresponding to the accumulated volume of milk which has flowed through the sensor since last reset thereof. In another embodiment the display monitor can show the volume of milk suckled in each segment of time since the initiation of the current breast feeding, the net accumulation of transferred milk, and other parametric aspects of the milk flow which can be deduced from the optical measurement.

DETAILED DESCRIPTION OF THE DRAWING

Figure 1:
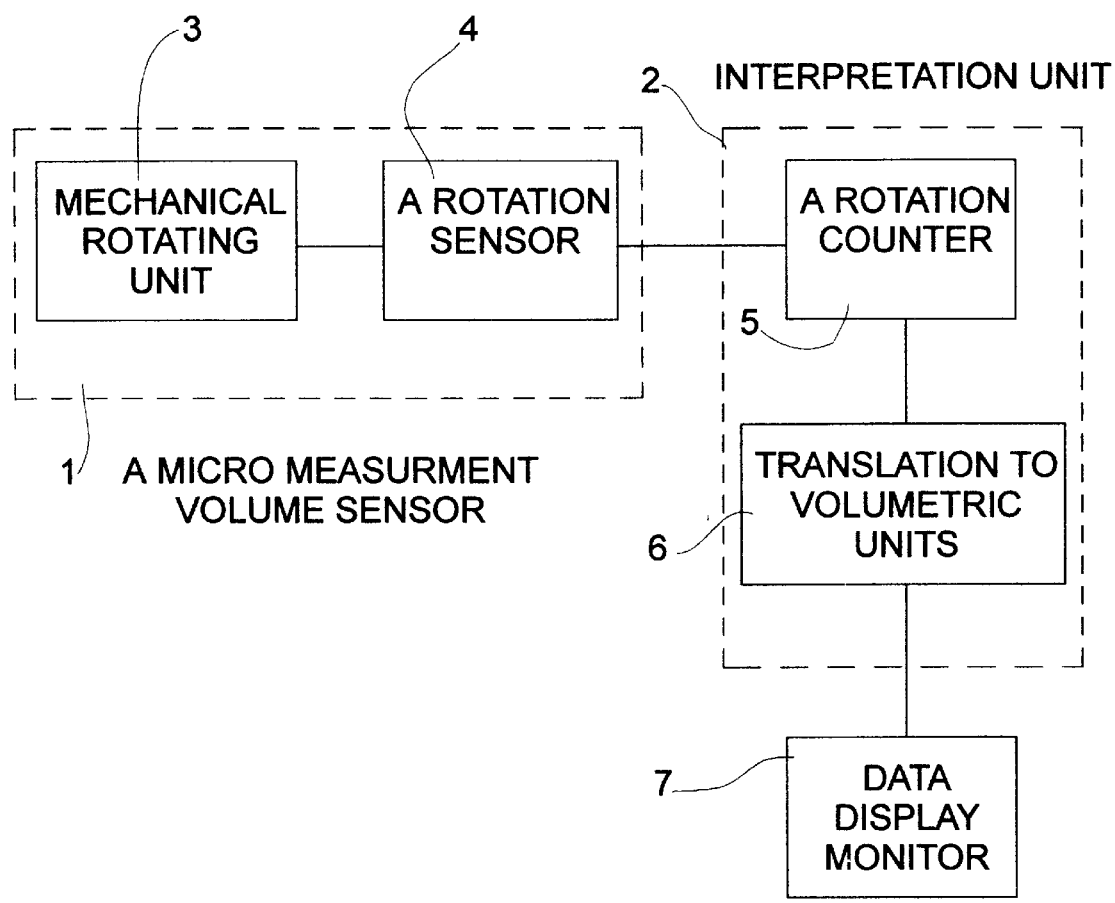
FIG. 1 is a block diagram of the logical steps in the method of monitoring milk volume according to the invention.

FIG. 1 illustrates a block diagram of the logical steps in the method of monitoring the milk volume wherein there is a micro measurement volume sensor (1) connected to an interpretation unit (2). The micro measurement volume sensor (1) contains a mechanical rotating unit (3) connected to a rotation sensor (4). The rotation sensor (4) is connected to the interpretation unit (2) and this interpretation unit contains a rotation counter (5) which passes data to a translator to volumetric units (6) and the results are displayed on the data display monitor (7). Thus the volume of milk which flows past the mechanical rotating unit (3) is expressed as a measured volume on the data display monitor (7).

Figure 2:
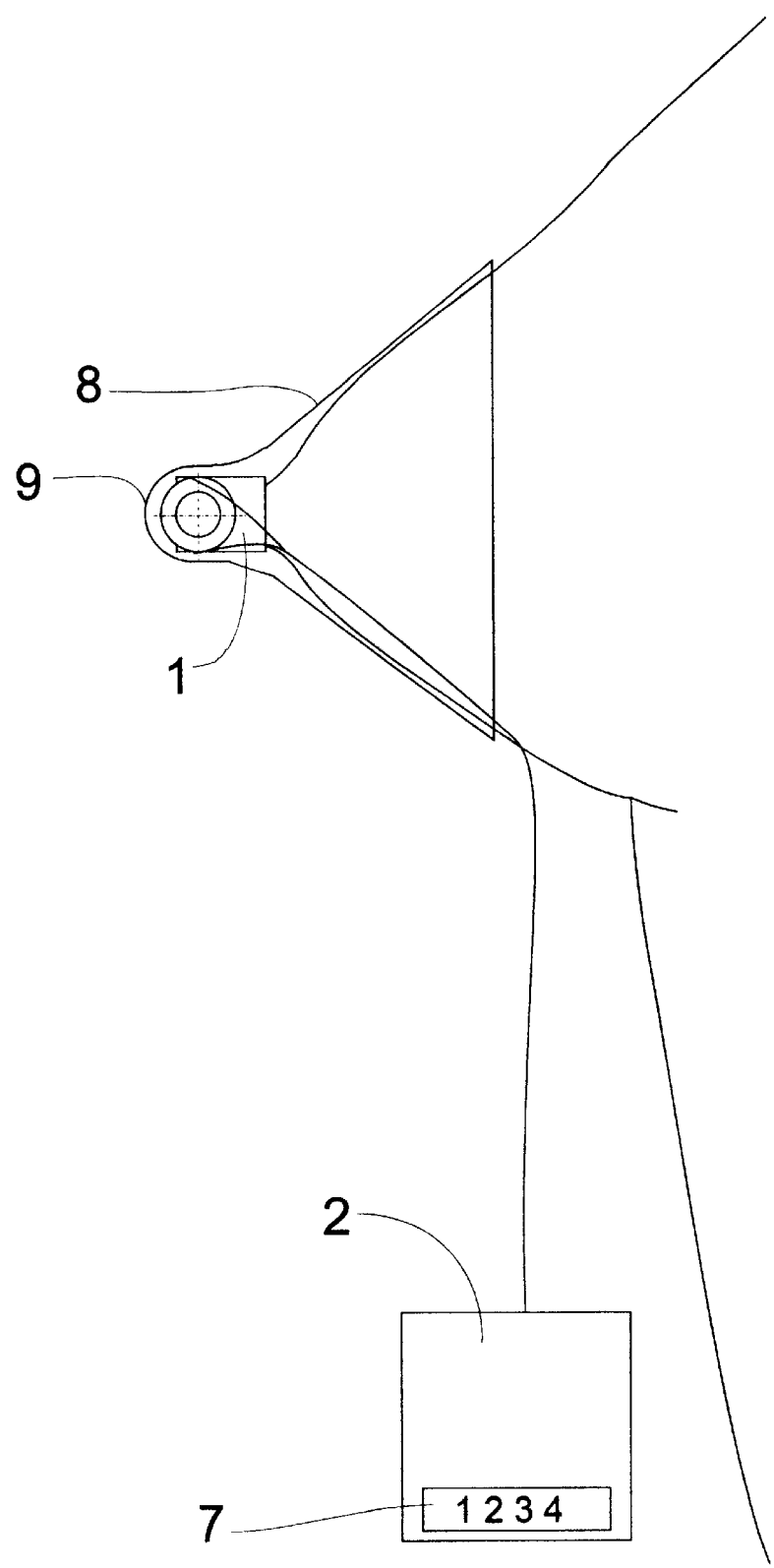
FIG. 2 illustrates a profile of the device according to the invention when adapted for use on the woman's breast.

FIG. 2 illustrates a profile of the device according to the invention when adapted for use on the woman's breast. A flexible elastic nipple cover (8) is designed like a nipple with holes (9) above the real nipple and is placed on the woman's breast above and arround the nipple. At the bottom of said cover in the space between the nipple and the elastic cover's holes there is a micro measurement volume sensor (1) for measuring the volume of the milk which flows through. This micro measurement volume sensor is connected to an interpretation unit (2) for counting and translating into volumetric units; and the data is then displayed on a data display monitor (7).

Figure 3:
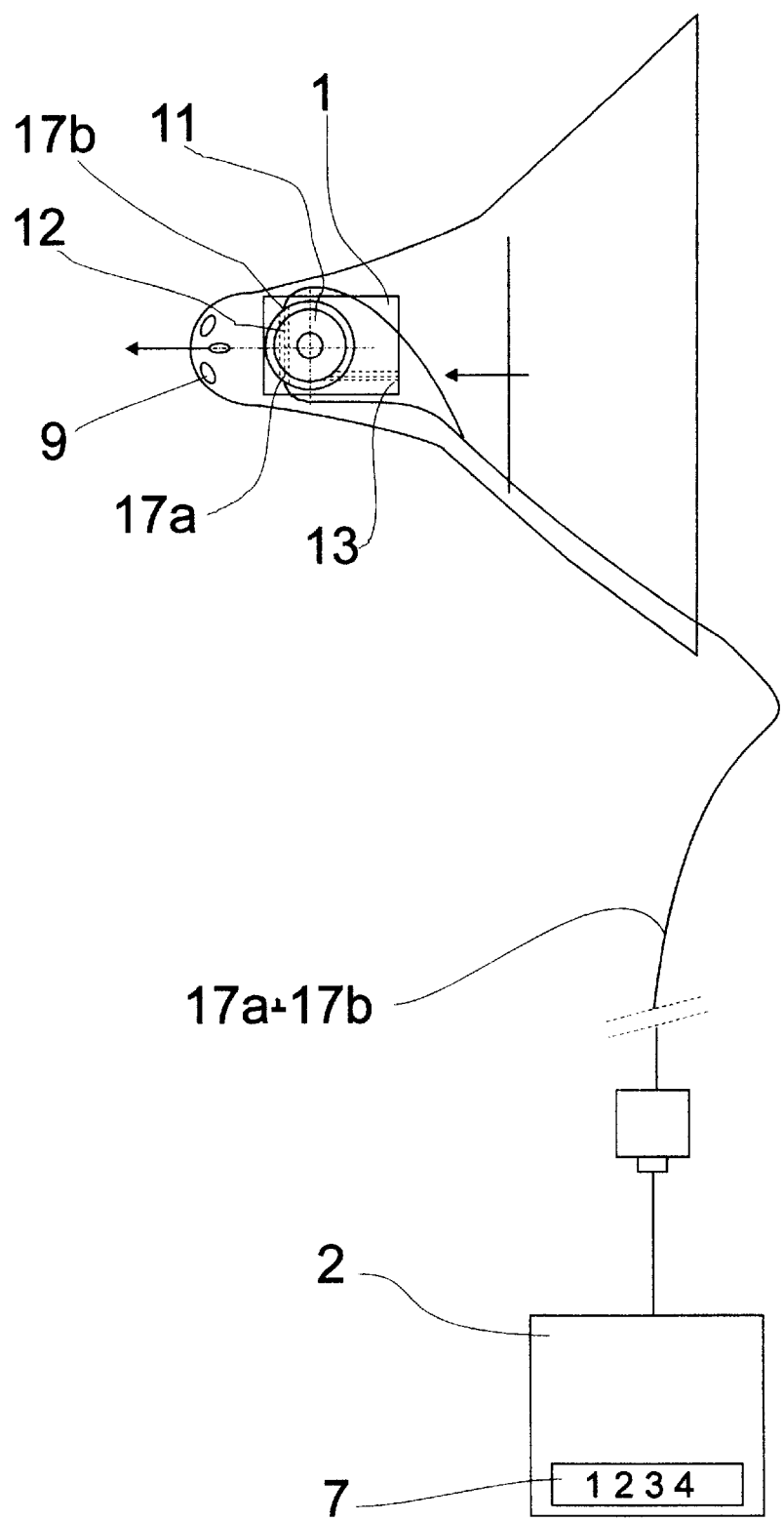
FIG. 3 is similar to FIG. 2 but shows an expanded and detailed view, especially of the micro measurement volume sensor.

FIG. 3 is the same as FIG. 2 but shows an expanded and detailed view especially of the micro measurement volume sensor (1). In the micro measurement volume sensor the milk flows through special passages (13) to a propeller (not seen in this figure) and causes the rotation of said propeller which in turn causes the rotation of a disk (11), attached to the propeller's axis, having an optic channel (12). This optic channel is connected on both sides to optic fibers (17a) (17b) where one optic fiber (17a) constantly illuminates and the other optic fiber (17b) receives the light pulses caused by the rotation of the disk (11).

Figure 4:
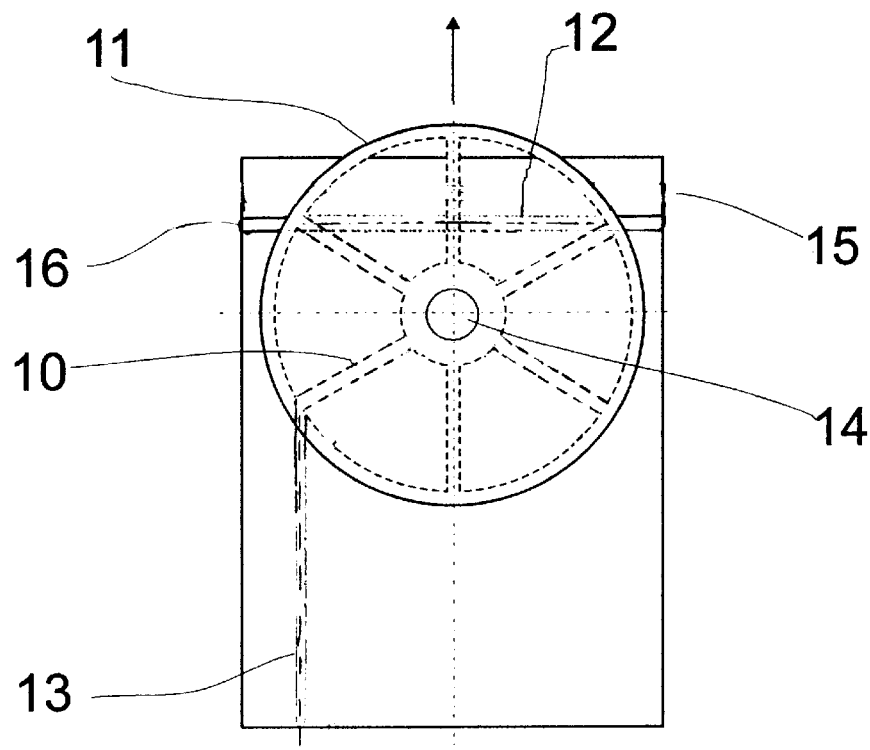
FIG. 4 illustrates a cross section of the micro measurement volume sensor.

FIG. 4 illustrates a cross section of the micro measurement volume sensor. Three passages (13) pass the milk exuded from the woman's nipple past a free spinning propeller (10) whose rotation is proportional to the amount of milk passing through. The propeller is rotating on an axis (14). This axis rotates a disk (11) at it's other end. This disk has an optic channel (12) which passes through a chord of the disk. In the fixed holder of said rotating disk there are two holes (15) (16) which are aligned with the optic channel of the disk. In every complete rotation of the disk there is one situation where the optic channel is aligned with the two holes (15) (16). Two optic sives (not shown in this figure) are to be connected to the holes (15) (16). One sive illuminates through hole (15) and the other sive receives this illumination after it has passed through the optic channel (12) and the other hole (16). Therefore there is one pulse of illumination for every cycle of the disk (11) and this disk's rotations are identical to the rotations of the propeller (10) because they are both connected to the same axis (14).

Figure 5:
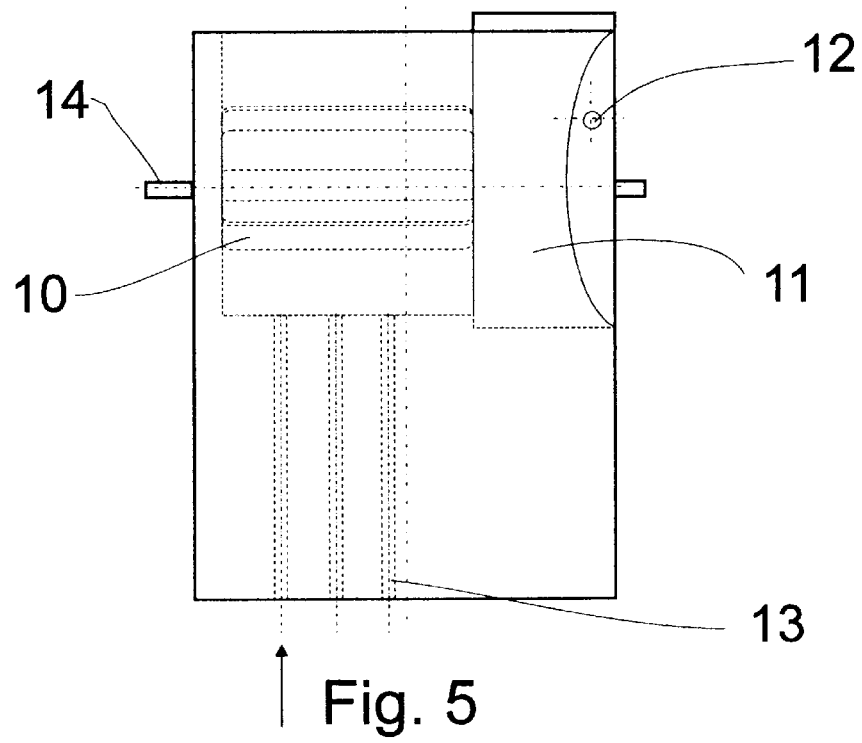
FIG. 5 illustrates another cross section of the micro measurement volume sensor.

FIG. 5 illustrates another cross section of the micro measurement volume sensor. Three passages (13) pass the milk exuded from the woman's nipple past a free spinning propeller (10) whose rotation is proportional to the amount of milk passing through. The propeller is rotating on an axis (14). This axis rotates a disk (11) at it's other end. This disk has an optic channel (12) which passes through a chord of the disk. In the fixed holder of said rotating disk there are two holes (15) (16) which are aligned with the optic channel of the disk. In every complete rotation of the disk there is one situation where the optic channel is aligned with the two holes (15) (16). Two optic sives (not shown in this figure) are to be connected to the holes (15) (16). One sive illuminates through hole (15) and the other sive receives this illumination after it has passed through the optic channel (12) and the other hole (16). Therefore there is one pulse of illumination for every cycle of the disk (11) and this disk's rotations are identicle to the rotations of the propeller (10) because they are both connected to the same axis (14).

I claim:

1. A method for monitoring a volume of milk during breast feeding comprising:
   (a) applying over a nipple area of the breast an elastic nipple shaped cover having holes positioned above the nipple area for milk passage to a baby's mouth, wherein at a bottom of said cover, in a space between the nipple and the elastic cover holes, there is a micro measurement volume sensor for measuring the milk volume which flows therethrough;
   (b) converting data from said micro measurement volume sensor into a calibrated volumetric equivalent corresponding to milk volume data indicative of the milk volume; and
   (c) displaying the milk volume data on a display monitor.

2. A method according to claim 1, wherein the micro measurement volume sensor is a free spinning propeller.

3. A method according to claim 2, wherein the free spinning propeller is sensed by optical sieves transmitting light to the sensor and receiving back modified light.

4. A method according to claim 3, wherein the modified light is achieved by allowing the light path to pass through a volume disk of the sensor which is connected to a propeller axis of the propeller and which passes one pulse of light for every one complete rotation of the propeller.

5. A method according to claim 2, wherein a fluid flow volume of milk is proportional to a number of rotations of the propeller in the micro measurement volume sensor.

6. A method according to claim 2, wherein a fluid flow volume of milk is proportional to a number of rotations of a disk connected to a propeller axis of the propeller.

7. A method according to claim 6, wherein said disk has an optic channel which passes through a chord of the disk.

8. A method according to claim 1, wherein the conversion of the data from the sensor into said calibrated volumetric equivalent is performed by a data interpretation unit.

9. A method according to claim 8, wherein light originating in the interpretation unit traverses a fiber optic cable which is connected to the micro measurement volume sensor where the light is interrupted or modified and returned back to the interpretation unit along a different fiber optic cable or along the same fiber optic cable.

10. A method according to claim 9, wherein the measurement of returned light is by a photo electric sensor used as a stroboscopic counter.

11. A method according to claim 9, wherein the measurement of returned light is made by interferometry.

12. A device for real time monitoring of a volume of milk during breast feeding, comprising:
   (a) a flexible elastic nipple cover shaped in the form of a nipple and including holes positionable above a breast nipple during use;
   (b) a micro measurement volume sensor positioned to measure the milk volume passing through a space between the nipple and the cover, said volume sensor being attached to the cover at a bottom side thereof above the nipple;

(c) a data interpretation unit connected to the volume sensor for counting, integrating, normalizing, and interpreting an output of the volume sensor into a volumetric equivalent for milk;

(d) a data display monitor connected to receive volumetric equivalent data from said data interpretation unit to display milk volume data of the milk measured.

13. A device according to claim 12, wherein said micro measurement volume sensor has a free spinning propeller whose rotation is sensed.

14. A device according to claim 13 wherein the rotation of the free spinning propeller is sensed by optical sieves transmitting light to the sensor and receiving back modified light.

15. A device according to claim 14, wherein the modified light is achieved by allowing a light path to pass through a sensor volume disk connected to a propeller axis of the propeller and which passes one pulse of light for every one complete rotation of the propeller.

16. A device according to claim 13, wherein milk flow volume in the micro measurement volume sensor is proportional to a number of rotations of a disk connected to a propeller axis of the propeller.

17. A device according to claim 16, wherein said disk has an optic channel which passes through a chord of the disk.

18. A device according to claim 12, wherein the milk flow volume in the micro measurement volume sensor is proportional to the number of rotations of the propeller in the micro measurement volume sensor.

19. A device according to claim 12, wherein light originating in the interpretation unit traverses a fiber optic cable which is connected to the micro measurement volume sensor where the light is interrupted or modified and returned back to the interpretation unit along a different fiber optic cable or along the same fiber optic cable.

20. A device according to claim 19, wherein the measurement of the returned light is by a photo electric sensor used as a stroboscopic counter.

21. A device according to claim 19, wherein the measurement of the returned light is made by interferometry.

* * * * *